United States Patent
Graβl

(10) Patent No.: US 8,112,140 B2
(45) Date of Patent: Feb. 7, 2012

(54) DEVICE FOR DETECTING AND TRANSMITTING ELECTRICAL PULSES

(75) Inventor: Thomas Graβl, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 364 days.

(21) Appl. No.: 12/188,327

(22) Filed: Aug. 8, 2008

(65) Prior Publication Data

US 2009/0093730 A1 Apr. 9, 2009

(30) Foreign Application Priority Data

Oct. 5, 2007 (DE) .......... 10 2007 047 690

(51) Int. Cl.
*A61N 5/04* (2006.01)

(52) U.S. Cl. ..................................... 600/382

(58) Field of Classification Search .......... 600/382–391, 600/395
See application file for complete search history.

(56) References Cited

U.S. PATENT DOCUMENTS

| | | | |
|---|---|---|---|
| 3,543,761 A * | 12/1970 | Bradley | 607/40 |
| 4,353,372 A * | 10/1982 | Ayer | 600/393 |
| 4,763,660 A * | 8/1988 | Kroll et al. | 600/391 |
| 5,191,886 A * | 3/1993 | Paeth et al. | 600/382 |
| 6,259,939 B1 * | 7/2001 | Rogel | 600/390 |
| 6,662,055 B1 * | 12/2003 | Prutchi | 607/122 |
| 2002/0072664 A1 * | 6/2002 | Katzenmaier et al. | 600/391 |

FOREIGN PATENT DOCUMENTS

DE 36 37 956 A1 6/1987

* cited by examiner

*Primary Examiner* — Niketa Patel
*Assistant Examiner* — Hiba El-Kaissi
(74) *Attorney, Agent, or Firm* — McGlew and Tuttle, P.C.

(57) ABSTRACT

A device for detecting and transmitting electrical pulses from the body surface of a patient to device processing the electrical pulses. The device for detecting includes at least two electrical leads of different lengths, at least one electrical insulating material surrounding the at least two electrical leads, a connecting port for connection to the device for processing the electrical pulses at one end of the at least two electrical leads and a recess in the electrical insulating material of the at least two electrical leads, so that an electric contact can be established with the skin surface of the patient. The two leads of different lengths have a ratio of the electrical resistance to the length of the leads and/or the ratio of the impedance to the length of the leads that is/are greater in the shorter lead than in the longer lead. With the construction artifacts caused by external sources of interference are easily filtered out and it can be manufactured at a low cost, so as to be employed for disposable use.

33 Claims, 1 Drawing Sheet

DEVICE FOR DETECTING AND TRANSMITTING ELECTRICAL PULSES

CROSS REFERENCE TO RELATED APPLICATIONS

This application claims the benefit of priority under 35 U.S.C. §119 of German Patent Application DE 10 2007 047 690.8 filed Oct. 5, 2007, the entire contents of which are incorporated herein by reference.

FIELD OF THE INVENTION

The present invention pertains to a device for detecting and transmitting electrical pulses from the body surface of a patient to a means for processing the electrical pulses, comprising at least two electrical leads, of which at least two electrical leads have different lengths; at least one electrical insulating material surrounds the at least two electrical leads; a connecting port for connection to the means processing the electrical pulses, and a recess in the electrical insulating material of the at least two electrical leads, so that an electrical contact can be established with the skin surface of the patient.

BACKGROUND OF THE INVENTION

Devices for detecting and transmitting electrical pulses, e.g., EEG (electroencephalogram), ECG (electrocardiogram) and EIT (electric impedance tomography) cables, are used, for example, for electrocardiological measurements on patients in order to obtain information on the performance of the heart. Contacts are placed for this on the skin surface. The sum of these individual potentials can be measured on the body surface, and these are measured signals with very low frequencies, e.g., ranging from 0.1 Hz to 140 Hz, in the nV and μA ranges. In addition, by supplying an a.c. current with a frequency of, e.g., 40 kHz, the respiration parameters can be determined according to the so-called impedance method by means of the device.

Prior-art EEG, ECG and EIT cables have multiple shielding against external interferences, especially electromagnetic interferences and currents (artifacts), which distort weak measured signals. However, such EEG, ECG and EIT cables are expensive to manufacture, so that these cannot be employed for disposable use in patients for economic reasons.

U.S. Pat. No. 4,353,372 discloses a device for detecting and transmitting electrical pulses. A plurality of electrical leads of different lengths with an electrical insulating material are fixed at a first end to a connecting port for connection to the means processing the electrical pulses. The second ends of the leads of different lengths are provided with contacts to be placed on the skin surface of a patient. Due to the different lengths of the leads, different electrical resistances are present between the electrodes and the connecting port. The electrical resistance of the leads is directly proportional to the length of the electrical leads, i.e., the ratio of the electrical resistance to the length of the leads is constant. External interferences, especially electromagnetic interferences, in the leads disadvantageously induce different electric voltages and currents (artifacts) in the leads because of the different electrical resistances, and these electric voltages and currents can be filtered out by the means processing the electrical pulses only partially at best, for example, by means of stored algorithms. Thus, reliable and certain medical evaluation of the measured signals is not guaranteed.

SUMMARY OF THE INVENTION

An object of the present invention is therefore to make available a device for detecting and transmitting electrical pulses, in which the artifacts caused by external sources of interference can be easily filtered out. Furthermore, the devices shall be able to be manufactured at a low cost, so that it can also be employed for disposable use for patients.

This object is accomplished with a device for detecting and transmitting electrical pulses from the body surface of a patient to a means processing the electrical pulses, comprising at least two electrical leads, of which at least two electrical leads have different lengths, at least one electrical insulating material surrounding the at least two electrical leads; a connecting port for connection to the means processing the electrical pulses preferably at one end of the at least two electrical leads, and a recess in the electrical insulating material of the at least two electrical leads, so that an electric contact can be established with the skin surface of the patient, wherein in at least two leads the ratio of the electrical resistance to the length of the leads and/or the ratio of the impedance to the length of the leads is greater in at least one shorter lead than in at least one longer lead.

The artifacts induced by external sources of interference can thus be filtered out by the means processing the electrical pulses, because approximately the same artifacts are induced in leads of different lengths as well.

In particular, at least two leads with different lengths have essentially the same electrical resistance and/or the same impedance.

In an additional embodiment, the electrical resistance and/or the impedance differ by less than 10% and especially by less than 1% to 5% in at least two leads with different lengths.

In an additional embodiment, the cross-sectional area in at least two leads of different lengths is smaller in at least one shorter lead than in at least one longer lead. Leads of a greater length have a correspondingly scaled, larger cross-sectional area than leads of a shorter length, so that leads of different lengths have, for example, essentially the same electrical resistance.

In at least two leads of different lengths, the width and/or thickness should preferably be selected to be smaller in at least one shorter lead than in at least one longer lead. Leads of a greater length have a correspondingly scaled, greater width and/or thickness than leads of a shorter length, so that leads of different lengths have, for example, essentially the same electrical resistance.

In another embodiment, the cross section is smaller in at least one shorter lead among at least two leads of different lengths than in at least one longer lead. Leads of a greater length have a correspondingly scaled, larger cross section than leads of a shorter length, so that leads of different lengths have, for example, essentially the same electrical resistance.

In an additional embodiment, the leads of different length consist of different materials with a corresponding resistivity. The resistivity of the material of shorter leads is greater than the resistivity of the material of longer leads. As a result, it is possible to attain, for example, essentially the same electrical resistance in leads of different lengths.

In an additional embodiment, an electrical resistor, i.e., an electrical or electronic component, is installed in at least one shorter lead. It is possible as a result to attain, for example, essentially the same electrical resistance in leads of different lengths.

The leads preferably consist of a metal or an alloy of metals, for example, aluminum, copper, gold, silver or tin.

In an additional embodiment, the leads consist of conductive plastic, graphite, carbon fibers or metallized polyamide (PA).

The leads are preferably manufactured from a metal foil or a metal plate.

In another embodiment, the metal paste is printed or screen printed.

In an additional embodiment, the at least two leads of different lengths are printed or screen-printed repeatedly to obtain different cross-sectional areas. The different cross-sectional areas of the leads can thus be obtained in an especially simple manner and at an especially low cost during the manufacture of the leads.

The distance between the leads preferably varies, for example, by at least one lead being arranged at a greater distance from the other leads than the other leads among each other or by one lead being bent especially in a serpentine shape. In particular, at least one lead has a substantially greater distance than the other leads among each other. The at least one lead with the substantially greater distance can be used for other purposes with a higher current demand than the other leads, which are used to conduct weak measured signals. The interferences originating from the leads for the higher current demand and acting on the other leads can thus be markedly reduced.

At least one lead preferably surrounds the other leads at least partially, so that the at least one lead is used, especially in case of grounding, to shield the other leads against interferences, especially electromagnetic interferences.

In another embodiment, two leads are designed as capacitors, especially in the area of the connecting port, preferably such that the surface of the leads is correspondingly tuned. The leads are made, for example, broader in order to obtain a capacitor with a sufficient capacity.

In an additional embodiment, at least one lead is designed as a coil, and two leads are preferably connected by means of an electrical contact into an electrical coil, especially in the area of the connecting port.

The cooperation of the capacitor formed by the leads and the electrical coil preferably embodies a filter, preferably a high-pass and/or low-pass filter, especially a low-pass filter with a limit frequency below 25 kHz. For example, artifacts from high-frequency surgical instruments can thus be filtered out.

In another embodiment, the cooperation of the capacitor formed by the leads and the electrical coil embodies an antenna for an RFID transponder.

In particular, the connecting port is designed as a transmitter for the wireless transmission of electrical pulses; in particular, the connecting port has an RFID transponder.

In another embodiment, the electrical contact with the skin surface of the patient can be established directly or indirectly by means of the at least one electrical lead at a recess in the electrical insulating material of the at least two electrical leads by an electrode being able to be detachably or nondetachably fastened to the at least one electrical lead.

In another embodiment, the insulating material consists of plastic and/or a foamed and/or textile material, e.g., polyester, Polyethylene (PE) foam or a synthetic faux fur. Polyester, preferably PE foam, makes possible a high level of wear comfort of the device for the patient, because the material can be made very soft by foaming. Furthermore, the dielectric constant of the device can be adapted by selecting the material and structure of the material. The device can be designed such that a required dielectric strength of at least 5 kV is satisfied. This is necessary especially in case of the simultaneous use of defibrillators at the patient.

In an additional embodiment, the device comprises a multilayer, flat band with at least two leads designed as strip conductors and at least one first and second non-conductive layer as an electrical insulating material for the strip conductors, where the at least two strip conductors are provided between the first and second non-conductive layers and are preferably positioned next to each other and wherein the first and second non-conductive layers are connected to one another such that the at least two strip conductors are arranged insulated against each other and at least one recess is provided in the area of the strip conductors in the band and/or in the at least one first and second non-conductive layers, so that a contact can be established with the skin surface of the patient.

A third and/or fourth conductive layer are preferably provided, in which case the third and/or fourth conductive layers surround the first and second non-conductive layers. The electrical pulses led from the body surface of a patient and transmitted via the strip conductors of the device are thus advantageously shielded against external interferences, especially electromagnetic interferences. To achieve optimal shielding, the third and fourth conductive layers may be advantageously connected in at least one position.

In another embodiment, the third and fourth conductive layers consist of a network of conductive fibers.

In an additional embodiment, the conductive fibers have a color marking, at least in one section of the respective third and fourth conductive layers.

In particular, the strip conductors are fixed to the connecting port.

In another embodiment, at least one perforation is provided between the insulated strip conductors. The strip conductors can be separated from one another as a result and positioned on the body surface of the patient corresponding to the necessary lead positions. The perforation is preferably designed in the form of elongated holes arranged one after another. For this application, the elongated holes are used to make possible the separation of the strip conductors without damage to the insulating material. Thus, repositioning of the electrodes becomes possible.

In an additional embodiment, the band has a plurality of folds, the folds being preferably directed at an angle of 60° to 120° in relation to the strip conductors. This makes possible an accordion-like arrangement of the band. The device can be made available to the user in a folded state, so that the user can pull the band apart corresponding to the height of the patient.

The above-described device can be used according to the present invention for transmitting electrical pulses from the body surface of a patient to an electrocardiograph for recording an electrocardiogram, to an EIT means or to an anesthesia monitoring means for determining the bispectral index.

An exemplary embodiment of the present invention will be described in more detail below with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
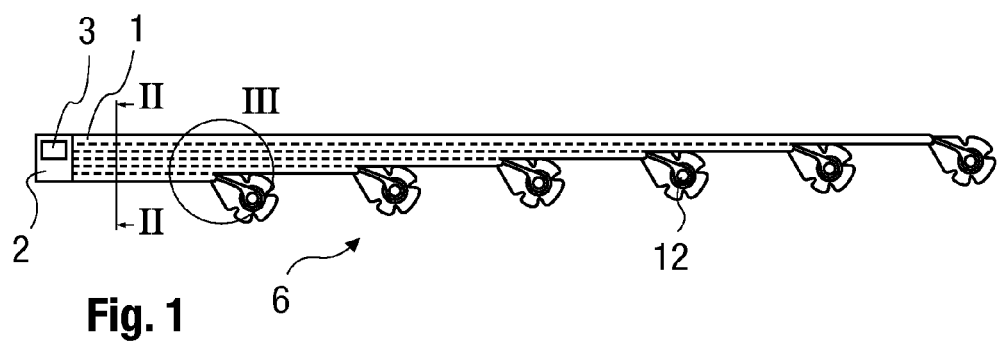
FIG. 1 is a simplified top view of the device according to the present invention.

Referring to the drawings in particular, FIG. 1 shows the device 6 according to the present invention for detecting and transmitting electrical pulses from the body surface of a patient, for example, to an electrocardiograph as a means (not shown) for processing electrical pulses. The device 6 comprises a multilayer band 1 with a connecting port 2. The connecting port 2 is provided to transmit the electrical pulses directly or via an adapter to the electrocardiograph. In another embodiment, the connecting port 2 may be designed as a transmitter for the wireless transmission of the electrical pulses. The connecting port 2 preferably has an RFID transponder 3, in which characteristic values of the device 6 are stored, so that automatic identification of the device 6 can be carried out at the electrocardiograph. However, characteristic values of the patients may also be stored in the RFID transponder 3, which makes it possible to unambiguously assign the electrical pulses to, e.g., data stored temporarily in the electrocardiograph.

Figure 2:
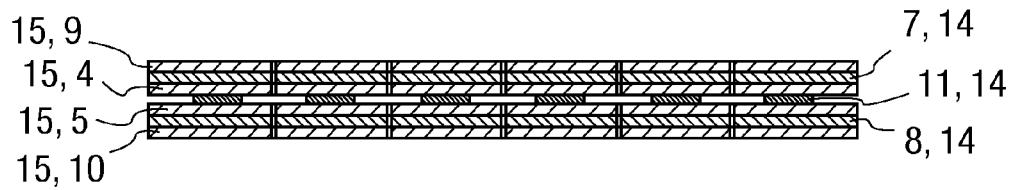
FIG. 2 is a schematic cross section B-B according to FIG. 1.

The band 1 is designed with first and second non-conductive layers 4, 5 (FIG. 2) made of polyester, preferably PE foam. The first and second non-conductive layers 4, 5 may also consist of polypropylene or polyurethane. Five leads 14 designed as strip conductors 11 are arranged next to each other between the first and second non-conductive layers 4, 5. The first and second non-conductive layers 4, 5 are provided as an insulating material 15. The first and second non-conductive layers 4, 5 are connected to one another such that the five strip conductors 11 are arranged insulated next to each other. The strip conductors 11 are fixed to the connecting port 2 (FIG. 2). A recess each is provided in the band 1 and/or in the non-conductive layer 4, 5, so that a contact can be established between each strip conductor 11 and the skin of the patient. The strip conductors 11 are designed each as large-area strip conductors in the form of an electrode 12 in the area of the recess. In another embodiment, the strip conductors 11 may have a possibility of connection to a separate electrode 12 each (not shown).

The strip conductors 11 have different lengths, because these connect, see FIG. 1, the electrodes 12 to the connecting port 2 at different distances. The strip conductors 11 consist of a conductive silver paste printed on the first or second non-conductive layer 4, 5 according to the screen printing process. The thickness of the strip conductors 11 can be varied by multiple printing with the same template. The thickness of the strip conductors 11 is designed to be such (not shown) that the electrical resistance and/or the electric impedance of the strip conductors 11 between the connecting port 2 and the electrodes 12 are essentially equal.

In another embodiment, the cross-sectional area is designed (not shown), for example, by means of a variable width of the strip conductors 11, such that the electrical resistance and/or the electric impedance of the strip conductors 11 between the connecting port 2 and the electrodes 12 are essentially equal. In an additional embodiment, the strip conductors 11 are placed with a correspondingly scaled cross-sectional area on the first non-conductive layer 4 made of plastic fibers, the second non-conductive layer 5 is subsequently applied, and the first and second non-conductive layers 4, 5 are connected hereafter by hot lamination.

Electric currents, hereinafter called artifacts, can be induced in the strip conductors 11 by external sources of interference, for example, a high-frequency surgical instrument or a cell phone. These artifacts are approximately equal in the strip conductors 11 of different lengths because of the essentially equal electrical resistance and/or the essentially equal electrical impedance of the strip conductors 11. This makes possible the complete or nearly complete, problem-free filtering of the artifacts by means of, for example, algorithms stored in the electrocardiograph. The medical evaluation and analysis of the measured signals, for example, of an ECG measurement, can thus be carried out securely and reliably even in case of external sources of interference because the electrocardiograph can filter out the induced artifacts.

Device 6 can be manufactured simply and inexpensively because of its construction and employed for disposable use for patients in hospitals. It is thus possible to carry out ECG, EEG and EIT measurements without distorting effects of sources of interference with such devices 6 as well.

In another embodiment, not shown, the strip conductors 11 may be designed at the connecting port 2 as a coil or a coil may be connected to at least one strip conductor 11. The remainder of one strip conductor 11 (the part of the strip conductor which is not the coil) can be connected to the coil by an electrical contact in an area of the connecting port 2. The electrical connection between two strip conductors 11 manufactured according to the screen printing process into a coil is carried out by means of a through hole plating hole, a so-called mat. The conductive silver paste is also introduced into the mat according to the screen printing process, so that there is an electrical connection between at least two strip conductors 11. In addition, at least two strip conductors 11 may be designed as a capacitor. The capacity of the capacitors can be adapted by a correspondingly designed width and/or length of the strip conductors 11. The capacitor may be connected to a coil and forms an electrical oscillating circuit. In particular, the electrical oscillating circuit is used as a filter for the selective filtering of electrical pulses, for example, as a low-pass filter for frequencies below 25 kHz.

In one embodiment, not shown, a bar code may be integrated in the first and/or second non-conductive layers 4, 5, preferably in the area of the connecting port 2. This makes possible the unambiguous identification of the device 6 and facilitates especially the logistics.

FIG. 2 shows the design of the multilayer flat band 1. A third and fourth conductive layers 7 and 8, which preferably consist of a network of conductive fibers, are provided around the first and second non-conductive layers 4 and 5. The conductive fibers may be provided with a color marking and thus facilitate the assignment of the individual electrodes 12 of the particular strip conductors 11 to the lead positions of the electrical pulses from the body surface of the patient. The electrical pulses led from the body surface of the patient and transmitted via the strip conductors 11 of the device 6 are advantageously shielded with the third and fourth conductive layers 7 and 8 against external interferences, especially electromagnetic interferences. The third and fourth conductive layers 7 and 8 may be advantageously connected to one another in at least one position in order to achieve optimization of the shielding and they are, in general, grounded.

The outer surfaces of band 1 are formed, as is shown in FIG. 2, by a fifth and sixth non-conductive layers 9 and 10 as an additional insulating material 15. Adhesive elements for adhering the electrodes 12 to the skin surface (not shown) are provided in the area of the electrodes 12 at the outer fifth and sixth non-conductive layers 9 and 10 of band 1. The non-conductive layers 4, 5, 9 and 10 are preferably designed based on their thickness such that they guarantee an overvoltage protection in the range of 5 kV.

Figure 3:
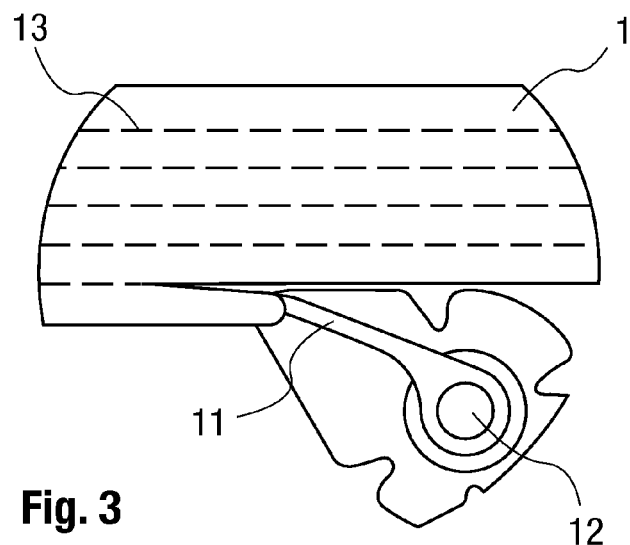
FIG. 3 is a schematic detail A according to FIG. 1 on a larger scale.

FIG. 3 shows perforations 13 between the insulated strip conductors 11, which are intended to partially separate the strip conductors 11 from one another and to make it possible to position them on the body surface of the patient corresponding to the necessary lead positions. The perforation 13 is preferably designed in the form of elongated holes between the insulated strip conductors 11. It will thus become possible to separate the strip conductors 11 without damage to the insulating material and thus to reposition the electrodes 12. In one embodiment, not shown, band 1 has a plurality of folds provided at right angles to the strip conductors 11. These folds make it possible to arrange the band 1 in the form of an accordion. The device 6 can be made available to the user in a folded state. The user can pull apart the device 6 corresponding to the height of the patient and thus place the electrodes 12 in exactly defined anatomic positions on the body surface of the patient.

On the whole, the embodiment of the device 6 according to the present invention, which is shown in FIGS. 1 through 3, makes available an ECG, EEG and EIT cable with integrated electrodes 12, which cable simplifies clinical processes because it is used only once per patient because of optimized manufacturing costs, can accompany the patient through the care areas from the emergency treatment to the intensive care unit via the operating room and, moreover, the artifacts induced by sources of interference in the electrocardiograph can be filtered out without problems, so that a medically safe and reliable analysis of the measured signals is possible.

While specific embodiments of the invention have been shown and described in detail to illustrate the application of the principles of the invention, it will be understood that the invention may be embodied otherwise without departing from such principles.

What is claimed is:

1. A device for detecting and transmitting electrical pulses from the body skin surface of a patient to an electrical pulse processor, the device comprising:
   two electrical leads of different lengths, each of said electrical leads having a total electrical resistance and impedance wherein one of a ratio of electrical resistance to the length of said leads and a ratio of the impedance to the length of said leads in said two electrical leads of different lengths is greater in at least a shorter of said two electrical leads than in a longer of said two electrical leads configured to cause said one of said total resistance and impedance of each of said leads to be closer to each other;
   a connecting port for connecting the device to the electrical pulse processor;
   at least one electrical insulating material surrounding said two electrical leads; and
   a recess in said electrical insulating material for electrical contact to be established with the skin surface of the patient.

2. A device in accordance with claim 1, wherein said two electrical leads of different lengths have essentially equal values of one of said total electrical resistance and impedance.

3. A device in accordance with claim 1, wherein said one of said total electrical resistance and impedance of said two electrical leads of different lengths differs by less than 10%.

4. A device in accordance with claim 1, wherein said one of said total electrical resistance and impedance of said two electrical leads of different lengths differs by less than 5%.

5. A device in accordance with claim 1, wherein a cross-sectional area in a shorter of said two electrical leads is smaller than a cross-sectional area in a longer of said two electrical leads.

6. A device in accordance with claim 1, wherein one of a width and a thickness in said shorter of said two electrical leads are smaller than in said longer of said two electrical leads.

7. A device in accordance with claim 1, wherein said two electrical leads consist of a metal or an alloy of metals aluminum, copper, gold, silver or tin.

8. A device in accordance with claim 7, wherein said two electrical leads are manufactured from a metal foil or a metal plate.

9. A device in accordance with claim 1, wherein said two electrical leads comprise metal paste printed or screen printed.

10. A device in accordance with claim 9, wherein said two electrical leads are formed from a plurality of layers configured to be repeatedly printed or screen printed to obtain different cross-sectional areas.

11. A device in accordance with claim 1, wherein said two electrical leads consist of conductive plastic, graphite, carbon fibers or metallized polyamide.

12. A device in accordance with claim 1, wherein the distance between said two electrical leads varies with at least one of:
   at least one said two electrical leads being arranged at a greater distance from another of said two electrical leads;
   said at least one said two electrical leads being bent relative to said another of said two electrical leads; and
   at least one said two electrical leads having a serpentine shape.

13. A device in accordance with claim 1, wherein at least one of said two electrical leads comprises a capacitor in an area of said connecting port such that said one lead is correspondingly tuned.

14. A device in accordance with claim 1, wherein:
   at least one of said two electrical leads comprises a coil and a remainder;
   an electrical contact connects said coil to said remainder in an area of said connecting port.

15. A device in accordance with claim 1, wherein:
   at least one of said two electrical leads comprises a capacitor in an area of said connecting port such that said one lead is correspondingly tuned;
   at least one of said two electrical leads comprises a coil and a remainder;
   an electrical contact connects said coil to said remainder in an area of said connecting port; and
   said capacitor and said coil are connected to form a low-pass filter with a limit frequency of 25 kHz.

16. A device in accordance with claim 1, wherein:
   at least one of said two electrical leads comprises a capacitor in an area of said connecting port such that said one lead is correspondingly tuned;
   at least one of said two electrical leads comprises a coil and a remainder;
   an electrical contact connects said coil to said remainder in an area of said connecting port; and
   said capacitor and said coil are connected to form an antenna of an RFID transponder.

17. A device in accordance with claim 1, wherein said connecting port comprises a transmitter for the wireless transmission of electrical pulses, said connecting port having a RFID transponder.

18. A device in accordance with claim 1, further comprising an electrode, wherein said electrical insulating material recess is provided for directly or indirectly establishing electrical contact with the skin surface of the patient with one of said two electrical leads, said electrode configured to attach detachably or nondetachably to said at least one of said two electrical leads.

19. A device in accordance with claim 1, wherein said insulating material consists of plastic and/or a foamed and/or textile material including one or more of polyester, Polyethylene (PE) foam or a synthetic faux fur.

20. A device in accordance with claim 1, wherein the electrical insulating material surrounding said two electrical leads comprises a multilayer flat band with said two electrical leads in the form of strip conductors and including at least one first and second non-conductive layer configured as electrical insulating material for said strip conductors, wherein said strip conductors are provided between said first and second non-conductive layers and are positioned next to each other, and wherein said first and second non-conductive layers are connected to one another such that said strip conductors are arranged insulated next to each other and said recess is provided in said band and/or in the at least one said first and second non-conductive layers in an area of said strip conductors whereby electrical contact can be established with the skin surface of the patient.

21. A device in accordance with claim 20, wherein a third and/or fourth conductive layers are provided, wherein said third and/or fourth conductive layers surround said first and second non-conductive layers.

22. A device in accordance with claim 20, wherein at least one perforation of elongated holes is provided between said insulated strip conductors.

23. A device in accordance with claim 20, wherein said band has a plurality of folds, said folds being directed at an angle of 60° to 120° in relation to said strip conductors.

24. A device in accordance with claim 1, wherein:
said first and second leads are receivable of artifacts induced by external sources of interference;
said one of said total resistance and said impedance of said first and second leads are chosen to have the induced artifacts to be approximately the same.

25. A device in accordance with claim 24, wherein:
the electrical signal processor includes a filter for filtering out equal artifacts in said leads.

26. A device in accordance with claim 1, wherein:
said first and second leads are formed of an electrically conductive material which causes a resistance of the leads to change as a function of said length of a respective said lead;
parameters of said first and second leads are different in said first and second leads in order to compensate for said resistance changes caused by different said lengths of said first and second leads.

27. A method for detecting and transmitting electrical pulses from the body skin surface, the method comprising the steps of:
providing two electrical leads of different lengths, whereby one of a ratio of electrical resistance to the length of said leads and a ratio of the impedance to the length of said leads in said two electrical leads of different lengths is greater in at least a shorter of said two electrical leads than in a longer of said two electrical leads to cause one of a total resistance and impedance of each of said leads to be closer to each other;
providing a connecting port for connecting a device to an electrical pulse processor;
surrounding said two electrical leads with electrical insulating material;
providing a recess in said electrical insulating material and establishing electrical contact with the skin surface of the patient;
transmitting electrical pulses from the body surface of a patient to an electrocardiograph for recording an electrocardiogram, an electroencephalogram, an electric impedance tomography device or an anesthesia monitoring means for determining a bispectral index.

28. A method in accordance with claim 27, wherein:
said first and second leads are receivable of artifacts induced by external sources of interference;
said one of said total resistance and impedance of said first and second leads are provided to have the induced artifacts in said first and second leads to be more similar.

29. A device for transferring electrical signals from a body of a patient to an electrical signal processor, the device comprising:
a connecting port adapted to connect to the electric signal processor;
a first electrical lead having one end connected to said connecting port, said first electrical lead having a first length, said first electrical lead being capable of receiving artifacts induced by external sources of interference, said first electrical lead having a feature which affects one of the total electrical resistance and impedance of said first lead;
a second electrical lead having one end connected to said connecting port, said second electrical lead having a second length different from said first length, said second electrical lead being capable of receiving artifacts induced by external sources of interference, said second electrical lead having a feature which affects one of the total electrical resistance and impedance of said second lead, said feature of said second lead being different from said feature of said first lead to have the induced artifacts in said first and second leads to be more similar
said first length is longer than said second length; said feature of said first lead causes a lower ratio of electrical resistance or impedance to length than said second feature;
electrical insulating material surrounding said first and second electrical leads, said electrical insulating material defining a recess for establishing electrical contact with the body of the patient.

30. A device in accordance with claim 29, wherein:
the induced artifacts depend on said one of the resistance and impedance of said leads;
said feature of said second lead is different from said feature of said first lead to cause said one of a total resistance and impedance of said second lead to be closer to one of a total resistance and impedance of said first lead than if said features were the same.

31. A device in accordance with claim 29, wherein:
each of said features is one of a cross sectional area, a type of said conductive material, and a shape of said conductive material.

32. A device in accordance with claim 30, wherein:
one of said electrical resistance and said electrical impedance of said first and second electrical leads are substantially equal.

33. A device in accordance with claim 30, wherein:
a difference between one of said electrical resistance and said electrical impedance in said first and second electrical leads is within 10%.

* * * * *